US011224437B2

(12) United States Patent
Rabkin et al.

(10) Patent No.: US 11,224,437 B2
(45) Date of Patent: Jan. 18, 2022

(54) SOFT EMBOLIC IMPLANT (71) Applicant: Penumbra, Inc., Alameda, CA (US)

(72) Inventors: Alexander Plagge Rabkin, San Francisco, CA (US); Stephen Pons, San Francisco, CA (US); Delilah Hui, American Canyon, CA (US)

(73) Assignee: Penumbra, Inc., Alameda, CA (US)

( * ) Notice: Subject to any disclaimer, the term of this patent is extended or adjusted under 35 U.S.C. 154(b) by 616 days.

(21) Appl. No.: 14/562,532

(22) Filed: Dec. 5, 2014

(65) Prior Publication Data
US 2015/0196304 A1 Jul. 16, 2015

Related U.S. Application Data (63) Continuation-in-part of application No. 14/154,395, filed on Jan. 14, 2014, now Pat. No. 10,548,606.

(51) Int. Cl.
*A61B 17/12* (2006.01)
*C22F 1/00* (2006.01)
*A61B 17/00* (2006.01)

(52) U.S. Cl.
CPC .... *A61B 17/12145* (2013.01); *A61B 17/1215* (2013.01); *A61B 17/12109* (2013.01);
(Continued)

(58) Field of Classification Search
CPC ........ A61B 17/12113; A61B 17/12145; A61B 17/12154; A61B 17/1215;
(Continued)

(56) References Cited

U.S. PATENT DOCUMENTS 5,122,136 A 6/1992 Guglielmi et al.
5,154,705 A 10/1992 Fleischhacker et al.
(Continued)

FOREIGN PATENT DOCUMENTS

CN 1298287 A 6/2001
CN 103356258 A 10/2013
(Continued)

OTHER PUBLICATIONS

Arko, et al. Endovascular repair reduces early and late morbidity compared to open surgery for abdominal aortic aneurysm. J Endovasc Ther. Dec. 2002;9(6):711-8.
(Continued)

*Primary Examiner* — Elizabeth Houston
*Assistant Examiner* — Lindsey Bachman
(74) *Attorney, Agent, or Firm* — Haley Guiliano LLP (57) ABSTRACT

Soft embolic implants exhibiting secondary shapes are disclosed. Some of the embolic implants exhibit progressively increasing softness from the distal end to the proximal end of the coil. The embolic implants have a primary coil, an optional second coil, a shape wire, and a stretch resistant fiber disposed in the lumen of the primary coil. An optional distal support wire is also disclosed. The embolic implants include a proximal constraint assembly configured to be releaseably retained by a delivery device. Disposed near each end of some of the implants are elliptical hole washers through which the shape wire and the stretch resistant fiber are threaded. The embolic implants have a primary, linear configuration for delivery through an implant tool, and a secondary configuration after deployment from the implant tool. The secondary shape can be J-shaped, helical, spherical, complex, or a combination of shapes.

14 Claims, 11 Drawing Sheets

(52) U.S. Cl.
CPC ........ *A61B 17/12113* (2013.01); *C22F 1/006* (2013.01); *A61B 17/12154* (2013.01); *A61B 2017/00526* (2013.01); *A61B 2017/00867* (2013.01); *Y10T 156/1002* (2015.01)

(58) Field of Classification Search
CPC ........ A61B 17/12109; A61B 17/12118; A61B 17/1214; A61F 6/20; A61F 6/22
See application file for complete search history.

(56) References Cited

U.S. PATENT DOCUMENTS

| | | | |
|---|---|---|---|
| 5,853,418 A | 12/1998 | Ken et al. | |
| 6,280,457 B1* | 8/2001 | Wallace | A61B 17/12022 606/191 |
| 6,638,291 B1* | 10/2003 | Ferrera | A61B 17/12022 606/191 |
| 7,166,122 B2* | 1/2007 | Aganon | A61B 17/12022 606/200 |
| 2004/0034378 A1 | 2/2004 | Monstadt et al. | |
| 2006/0100661 A1 | 5/2006 | Jaeger et al. | |
| 2008/0103585 A1 | 5/2008 | Monstadt et al. | |
| 2008/0306503 A1 | 12/2008 | Que et al. | |
| 2009/0062812 A1 | 3/2009 | Fitz et al. | |
| 2010/0076479 A1 | 3/2010 | Monstadt | |
| 2010/0137898 A1* | 6/2010 | Teoh | A61B 17/12022 606/195 |
| 2010/0174301 A1 | 7/2010 | Wallace et al. | |
| 2010/0268204 A1* | 10/2010 | Tieu | A61B 17/12022 606/27 |
| 2011/0184454 A1* | 7/2011 | Barry | A61B 17/12022 606/200 |
| 2012/0078285 A1 | 3/2012 | Griffin | |
| 2012/0089174 A1* | 4/2012 | Chen | A61B 17/12109 606/200 |
| 2012/0209310 A1* | 8/2012 | Chen | A61B 17/12022 606/195 |
| 2013/0190801 A1* | 7/2013 | Divino | A61B 17/12154 606/200 |
| 2013/0261659 A1 | 10/2013 | Lorenzo | |
| 2013/0331882 A1 | 12/2013 | Tompkins et al. | |
| 2014/0128907 A1 | 5/2014 | Hui et al. | |
| 2014/0277100 A1* | 9/2014 | Kang | A61B 17/12113 606/200 |

FOREIGN PATENT DOCUMENTS

| | | |
|---|---|---|
| EP | 1889577 A1 | 2/2008 |
| EP | 2505150 A1 | 10/2012 |
| EP | 2644129 A2 | 10/2013 |
| EP | 2674114 A1 | 12/2013 |
| JP | 2003501131 A | 1/2003 |
| JP | 2004500929 A | 1/2004 |
| JP | 2005533615 A | 11/2005 |
| WO | WO-2008112435 A2 | 9/2008 |
| WO | WO 2010/096541 A1 | 8/2010 |
| WO | WO-2015109007 A1 | 7/2015 |

OTHER PUBLICATIONS

International search report and written opinion dated May 5, 2015 for PCT/US2015/011449.
European Search Report dated Jun. 20, 2017 for EP Application No. 15737622.9.
Office Action dated Aug. 9, 2017 for U.S. Appl. No. 14/154,395.
U.S. Appl. No. 14/154,395 Office Action dated Jan. 24, 2018.
"Office action dated Aug. 9, 2018 for U.S. Appl. No. 14/562,532".
Final Office action dated Mar. 8, 2019 for U.S. Appl. No. 14/154,395.

\* cited by examiner

SOFT EMBOLIC IMPLANT

CROSS-REFERENCE TO RELATED APPLICATIONS

This application is a continuation-in-part of U.S. patent application Ser. No. 14/154,395, filed Jan. 14, 2014, now U.S. Pat. No. 10,548,606 the entire content of which is incorporated herein by reference.

FIELD OF THE INVENTION

The present invention relates generally to the field of medical treatment, and more particularly to an embolic implant or embolic coil for occluding an aneurysm or a blood vessel.

BACKGROUND OF THE INVENTION

Coil embolization is a commonly practiced technique for treatment of brain aneurysm, arterio-venous malformation, and other conditions for which vessel occlusion is a desired treatment option, such as, for example, in the occlusion of a tumor "feeder" vessel. A typical occlusion coil is a wire coil having an elongate primary shape with windings coiled around a longitudinal axis. In a typical aneurysm coil embolization procedure, a catheter is introduced into the femoral artery and navigated through the vascular system under fluoroscopic visualization. The coil in its primary shape is positioned within the catheter. The catheter distal end is positioned at the site of an aneurysm within the brain. The coil is passed from the catheter into the aneurysm. Once released from the catheter, the coil assumes a secondary shape selected to optimize filling of the aneurysm cavity. Multiple coils may be introduced into a single aneurysm cavity for optimal filling of the cavity. The deployed coils serve to block blood flow into the aneurysm and reinforce the aneurysm against rupture. While the overall device is commonly referred to as a coil, some of the individual components of the device are also referred to as coils. For clarity, the device herein will most often be referred to as an embolic implant, though it will be understood that the terms embolic coil and embolic implant are interchangeable.

DETAILED DESCRIPTION OF THE INVENTION

Some embodiments of the invention are described below. For clarity, not all features of each actual implementation are described in this specification. In the development of an actual device, some modifications may be made that result in an embodiment that still falls within the scope of the invention.

Figure 1A:
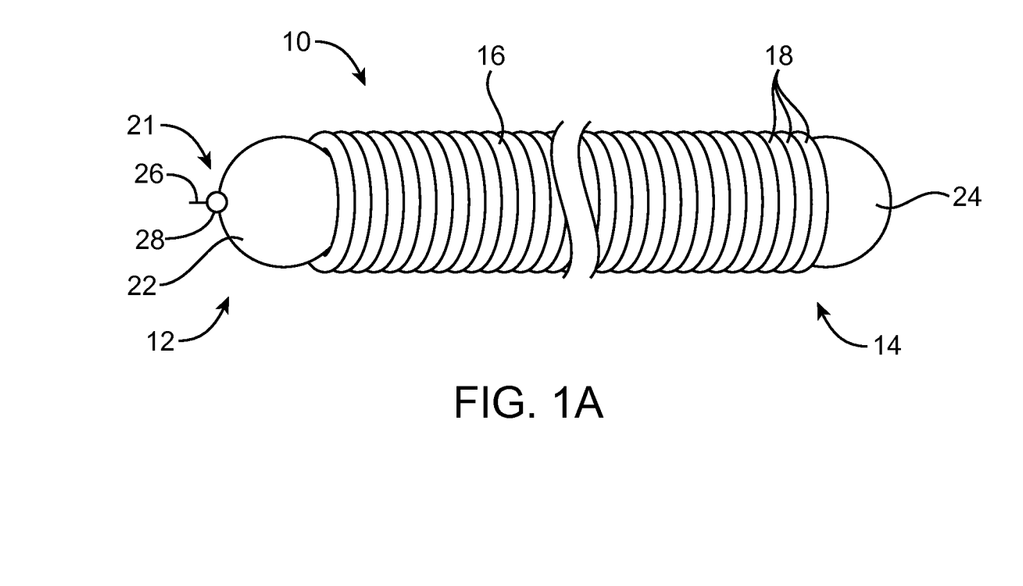
FIG. 1a is a side elevation view of an embodiment according to the invention, the embodiment illustrated in its delivery configuration.

Beginning with FIG. 1a, an embolic implant according to the invention is illustrated. Embolic implant 10 is shown in its linear, primary shape, from a side elevation view. Embolic implant 10 extends from its proximal end 12 to its distal end 14. Embolic implant 10 is an elongate device of considerable length, but the illustration of FIG. 1 is truncated, so that the device's features can be enlarged to show detail. In the illustration of FIG. 1, primary coil 16 is visible. Primary coil 16 is formed of a wire coiled to have a primary coil diameter D1 of approximately 0.012 inches, although smaller diameters, and diameters as large as 0.035 inches, may instead be used. The pitch of the coil may be uniform as shown, or it may vary along the length of the coil, or different sections of the coil may be formed to have different pitches. The wire material selected for the coil is preferably one capable of fluoroscopic visualization, such as Platinum, Platinum/Iridium, Platinum/Tungsten, Palladium, or other suitable material. In one embodiment, the wire forming the coil has a diameter of approximately 0.0010-0.0020 inches. Primary coil 16 is formed from continuous turnings of a wire or other filament to form windings 18, which extend essentially the length of primary coil 16, from proximal end 12 to distal end 14. Primary coil 16 terminates near distal end 14 in distal tip 24. Distal tip 24 is constructed to provide an atraumatic tip at the leading end, or distal end 14 of embolic implant 10. The portion of distal tip 24 that is visible in FIG. 1a can be molded or extruded from a suitable polymer such as polyester, low density polyethylene (LDPE), acrylic adhesive, or other material. Various alternative constructions of a distal tip according to the invention are discussed in detail below.

Also visible in FIG. 1a is proximal assembly 21. Proximal assembly 21, disposed at proximal end 12, is made up of proximal constraint sphere 22, fiber 26, and knot 28. Proximal assembly 21 and various alternative embodiments of a proximal assembly will be discussed in greater detail below. Proximal constraint sphere 22 can be fabricated from stainless steel, a polymer, or any other suitable material. Fiber 26 can be fabricated from polyethylene, ultra high molecular weight polyethylene (UHMWPE), polypropylene, or other suitable material. While the term "sphere" is used throughout this disclosure, it will be understood that in an alternative embodiment according to the invention may have a proximal constraint element that is not spherical. A proximal constraint element may be less than perfectly spherical, elliptic, cubic, or other suitable shape. A proximal constraint element according to the invention is configured to be releaseably retained by a delivery device (not pictured).

Figure 1B:
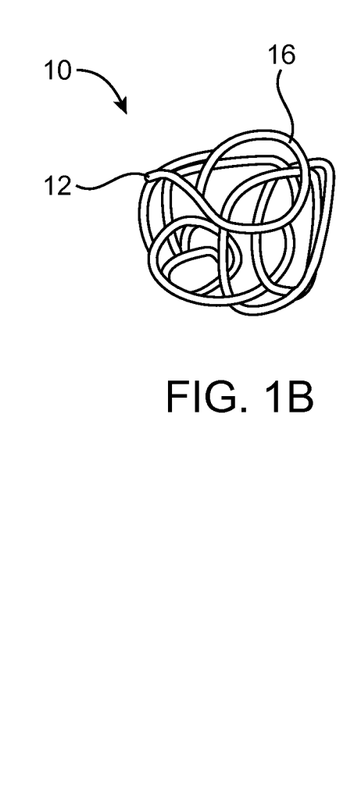
FIG. 1b is a side elevation view of the embodiment of FIG. 1a, the device in its secondary configuration.

As mentioned above, embolic implant 10 is shown in its linear, delivery configuration. Embolic implant 10 may be delivered into the vasculature of a subject via a delivery catheter or comparable implant tool (not pictured), while embolic coil or embolic implant 10 is in its delivery configuration. Once delivered to a treatment site within the vasculature, embolic implant 10 will be released from the delivery system, and will revert to a secondary configuration. A secondary configuration according to the invention may be curved, hooked, J-shaped, spiral, helical, complex, spherical, or any other desirable three dimensional configuration. In the example of embolic implant 10, the secondary configuration is complex. Embolic implant 10 is illustrated in its complex secondary configuration in FIG. 1b. In FIG. 1b, embolic implant 10 is no longer in a linear configuration, but rather is coiled or turned about itself in a complex, three dimensional array. The three dimensional array is advantageous for distributing the implant in a manner that will occlude blood flow in a vessel or in an aneurysm. Primary coil 16 and proximal end 12 are visible in FIG. 1b.

Figure 2:
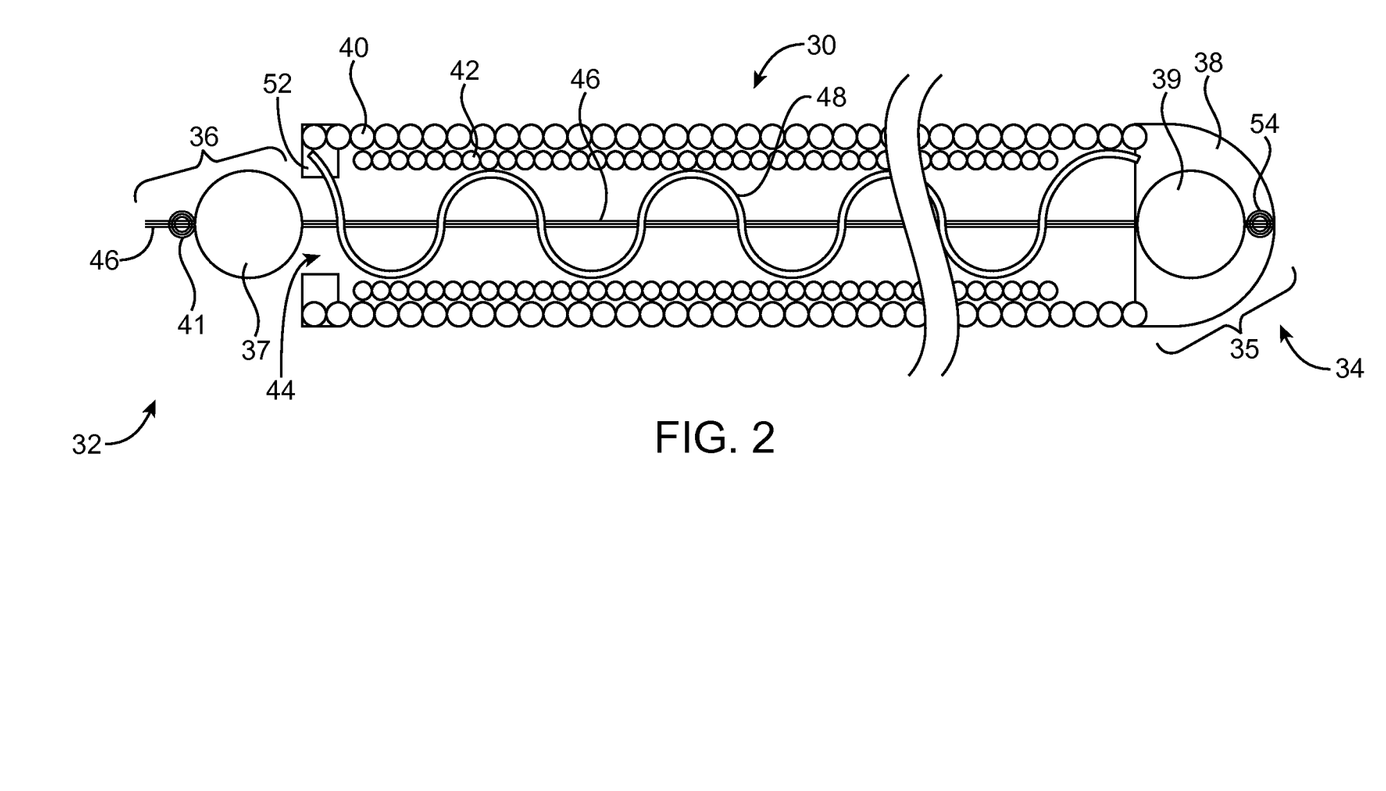
FIG. 2 is a cutaway side elevation view of an embodiment according to the invention, the embodiment in its delivery configuration.
Figure 11:
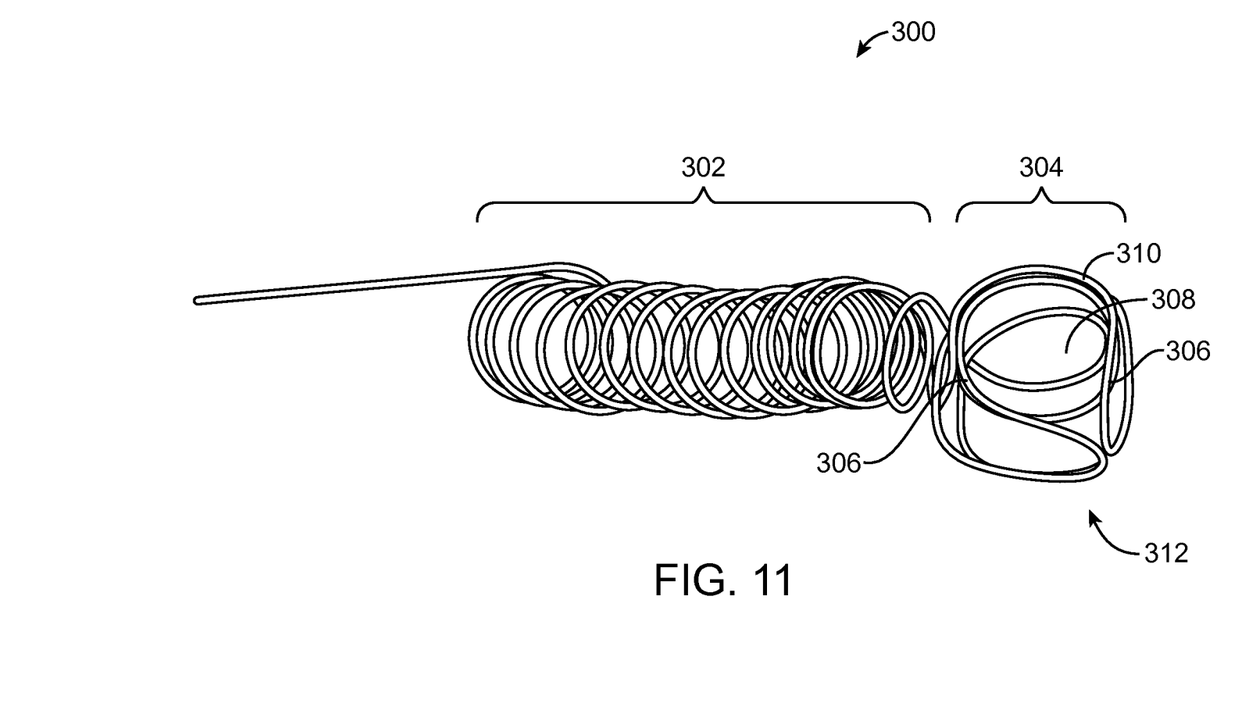
FIG. 11 is a plan view of an embodiment according to the invention, the embodiment shown in a deployed configuration, outside of a vessel of a subject.

Referring now to FIG. 2, a cutaway side view reveals some of the details of embolic implant 30. In FIG. 2, embolic implant 30 is illustrated in its primary delivery shape or configuration. In use, embolic implant 30 is constrained in and delivered in its primary configuration via a catheter delivery system. As embolic implant 30 is deployed from the distal end of a catheter, it will revert to its secondary configuration. A secondary configuration according to the invention may be curved, hooked, J-shaped, spiral, helical, complex, or any three dimensional configuration that is suitable for the therapeutic objectives for use of the device. An example of a complex configuration according to the invention is illustrated in FIG. 11, and described in detail below.

In the delivery configuration illustrated in FIG. 2, embolic implant 30 has a proximal end 32 and a distal end 34. A primary coil 40 and an inner coil 42 extend from the proximal end 32 to the distal end 34, and surround lumen 44. Primary coil 40 is constructed of thin Platinum wire, and inner coil is constructed of soft, kink resistant Nitinol. Disposed at proximal end 32 of embolic implant 30 is proximal constraint assembly 36. Proximal constraint assembly 36 is made of proximal constraint sphere 37, fiber 46, and knot 41. Proximal constraint sphere 37 may be constructed from gold or tin solder, Platinum, Titanium, stainless steel, or other suitable material. Proximal bond 52 is disposed in an annular fashion near proximal end 32, may be formed from polyester, acrylic adhesive, or other suitable material. The material forming proximal bond 52 may be reflowed or otherwise molded around the proximal end of primary coil 40. Proximal assembly 36 prevents proximal constraint sphere 37 from entering lumen 44. Proximal constraint sphere 37 also plays a role in the delivery of embolic implant 30, and is configured to be releaseably retained by a delivery tool or device such as those disclosed in U.S. patent application Ser. No. 14/460,234.

Disposed at distal end 34 is distal assembly 35. Defining distal assembly 35 are distal tip 38, distal sphere 39, and distal knot 54. Within lumen 44, and extending the length of lumen 44, is fiber 46. In addition to being disposed in lumen 44, fiber 46 is disposed within and through an internal channel or through hole (not visible) of proximal constraint element or proximal constraint sphere 37.

Fiber thus extends proximally through lumen 44, through proximal constraint sphere 37, and out of proximal constraint sphere 37 at proximal end 32. Fiber 46 is knotted to form proximal knot 41. Fiber 46 is thus anchored at the proximal end 32. Proceeding in the opposite direction, fiber 46 extends distally of proximal constraint element 37, through lumen 44, and through distal sphere 39, which has, similar to proximal constraint sphere 37, an internal channel or through hole (not visible in FIG. 2). During construction of implant 30, fiber 46 is also knotted to form distal knot 54. Fiber 46 is thus anchored at distal end 34. Fiber 46 is stretch resistant, and may be constructed from a suitable polymer such as polyethylene, ultra high molecular weight polyethylene (UHMWPE), polypropylene, or other suitable material. Because fiber 46 is stretch resistant, it will prevent stretching of primary coil 40 and inner coil 42, stretching which could potentially plastically deform the coils and interfere with the retractability of embolic implant 30 within a catheter, and potentially interfere with the ability of embolic implant 30 to reconfigure from its linear delivery configuration to its secondary configuration.

Distal sphere 39, which also may in the alternative have different shape, is retained by atraumatic distal tip 38. Atraumatic distal tip 38 is formed from a polymeric material such as polyester, an acrylic adhesive, or other suitable material. The material is injected, molded, reflowed, extruded, or otherwise placed around distal sphere 39, fiber 46 and distal knot 54 to securely bond the components one to another and to form an atraumatic distal tip. The embedding or other retention of distal sphere 39 also serves to prevent distal sphere 39 from entering lumen 44. Distal assembly 35, in conjunction with proximal assembly 36, thereby maintains tension upon fiber 46, and helps prevent stretching and distortion of primary coil 40 and inner coil 42.

Also disposed in lumen 44 is shape wire 48. Shape wire 48 is anchored in and extends from proximal bond 52, through lumen 44, and to distal tip 38. Wire 48 is formed from Nitinol or another suitable shape memory material. Wire 48 confers the desired complex secondary configuration on embolic coil 30. The proximal end of shape wire 48 is retained by proximal bond 52. The distal end of shape wire 48 is anchored to or secured by atraumatic distal tip 38. Because shape wire 48 is constructed of Nitinol, it is highly kink resistant, and confers softness on embolic implant 30, while at the same time reliably conferring a desired secondary shape on embolic implant 30. In the alternative, a relatively thin platinum wire may be used to construct primary coil 40, also conferring softness on embolic implant 30, enhancing the safety of the device.

In an alternative embodiment (not pictured), shape wire 48 may be ground or otherwise formed so that it is of a smaller diameter at its proximal end relative to its distal end. The diameter of shape wire 48 may increase gradually or incrementally from proximal end 32 to distal end 34. The resulting embolic coil would be of a more robust or a stiffer secondary shape at the distal end and a softer coil near the proximal end. The largest shape wire diameter would be a diameter based upon the level of robustness desired at the distal end of the device.

Alternative embodiments of the invention described above are illustrated in FIGS. 3-10. The embolic coils or embolic implants described below and illustrated in the figures have some elements in common with the embodiment illustrated in FIG. 2, though some of the common elements are arranged in alternative configurations than the configuration of FIG. 2. In order to be concise, the description of every detail of each element will not be repeated for each embodiment.

Figure 3:
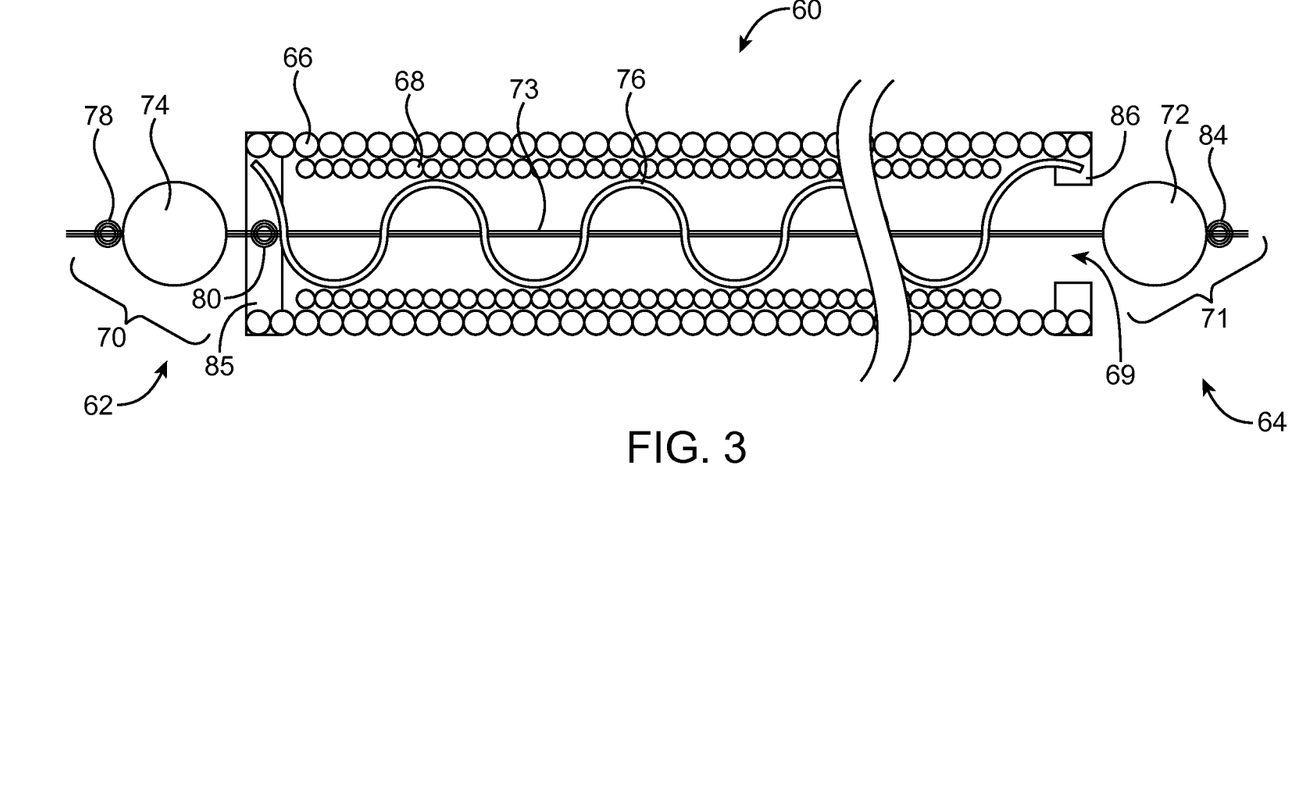
FIG. 3 is a cutaway side elevation view of an alternative embodiment according to the invention, the embodiment illustrated in its delivery configuration.

The embodiment illustrated in FIG. 3 will now be described. Embolic implant 60 has a proximal end 62 and a distal end 64. Embolic implant 60 includes primary coil 66 and optional inner coil 68, both of which surround lumen 69. In the embodiment of FIG. 3, primary coil 66 is constructed of Platinum, and inner coil 68 is constructed of Nitinol, though the coils may be constructed of other suitable materials and remain within the scope of the invention. Inner coil 68 may optionally be processed to impart shape memory characteristics. Proximal constraint assembly 70 is disposed at proximal end 62. Fiber 73 is threaded through a through hole (not visible) of proximal sphere 74, and knotted to form a first proximal knot 78. Fiber 73 is also knotted to form a second proximal knot 80. In an alternative embodiment, second proximal knot 80 is formed distal of the proximal end of coil 66, permitting some sliding movement of proximal constraint assembly 70. This sliding movement would be limited by proximal sphere 74 and knot 80. After formation of second proximal knot 80, during construction of implant 60, polyester, or an acrylic adhesive is reflowed, molded, or otherwise disposed at the proximal end of primary coil 66, to form proximal bond 85. Proximal bond 85 is a solid structure that anchors or secures fiber 73 and second proximal knot 80. Proximal bond 85, proximal sphere 74, fiber 73, first proximal knot 78, and second proximal knot 80 together define proximal constraint assembly 70. Proximal bond 85 prevents proximal constraint sphere 74 from entering lumen 69, helping to maintain tension on fiber 73, and preventing stretching and deformation of primary coil 66 and secondary coil 68.

Also secured by or anchored to proximal bond 85, and extending distally through lumen 69, is shape wire 76. Wire 76 is embedded in or otherwise bonded to proximal bond 85 near proximal end 62. Shape wire 76 is processed to impart a secondary shape on embolic implant 60. The profile of shape wire 76 may be altered to exhibit either a consistent or varied profile along its length. A larger profile shape wire will exhibit a more robust shape, and a smaller profile shape wire will exhibit a softer coil. Shape wire 76 extends distally and is anchored to distal bond 86. Distal bond 86 may be formed using similar techniques as those used to form proximal bond 85. However, in the implant 60, distal bond 86 defines a more ring-like structure than proximal bond 85. Distal bond 86 surrounds the distal end of primary coil 66.

Fiber 73 also extends distally, through lumen 69, and through a through hole of distal sphere 72. Fiber 73 is knotted to form distal knot 84 near distal end 64. Distal bond 86 prevents distal sphere 72 from entering lumen 69 at distal end 64. Both proximal bond 85 and distal bond 86 serve to maintain tension in stretch resistant member 73, and to prevent stretching and potential elongation of primary coil 66 and inner coil 68.

As mentioned above, prior to assembly of embolic implant 60, a secondary configuration is conferred upon wire 76. However, embolic implant 60 and wire 76 are constrained in a generally linear, or delivery configuration by a delivery catheter or comparable device so that embolic coil 60 may be delivered intravascularly. After delivery of embolic implant 60 to a vessel or within an aneurysm of a subject, wire 76 will revert from its linear delivery configuration to its secondary configuration (not pictured). Consequently, embolic implant 60 will also revert to its secondary configuration, such as, for example, the configuration illustrated in FIG. 1b above.

Figure 4:
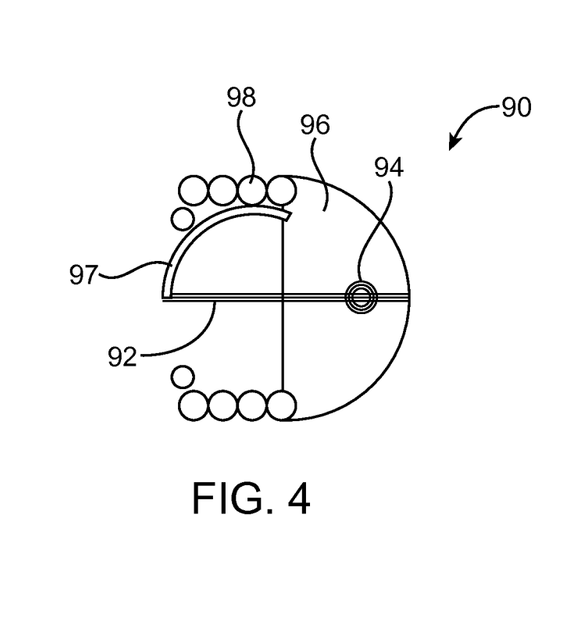
FIG. 4 is cutaway side view of a distal component of an embodiment according to the invention.

FIG. 4 illustrates a component of an alternative embodiment according to the invention. FIG. 4 illustrates only the distal assembly 90, which in use would be disposed at the distal end of an embolic implant according to the invention. Distal assembly 90 can be used as an alternative to the distal assemblies illustrated in FIGS. 2-3, in the fabrication of an embolic coil or embolic implant. Distal assembly 90 includes the distal end of fiber 92. Fiber 92 is knotted to form distal knot 94. Material such as polyester, acrylic adhesive, or other suitable material is reflowed, molded, injected, or otherwise formed around fiber 92 and distal knot 94 to form atraumatic distal tip 96. Distal tip 96 secures or anchors fiber 92 and distal knot 94, maintaining tension on fiber 92. Distal tip 96 also bonds to the distal end of primary coil 98, a portion of which is shown in FIG. 4, and to the distal end of shape wire 97, to together form a component of distal assembly 90.

Figure 5:
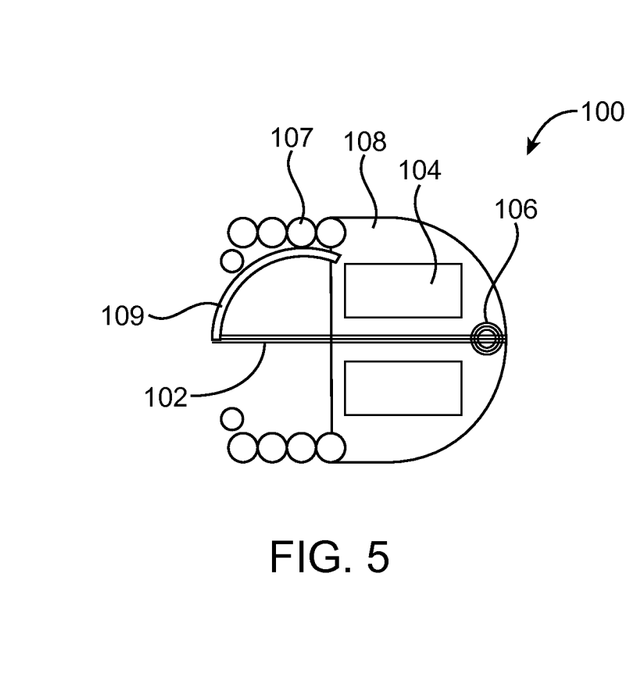
FIG. 5 is a cutaway side view of a distal component of an alternative embodiment according to the invention.

FIG. 5 illustrates yet another alternative embodiment of a distal assembly according to the invention. Distal assembly 100 includes fiber 102. Fiber 102 is passed through a tubing segment 104 and knotted to form distal knot 106. Distal tip 108 is formed from a cured material such as polyester, acrylic adhesive, or other suitable material that is reflowed, molded, injected, or otherwise placed around and bonded with tubing segment 104, fiber 102, the distal end of primary coil 107, and distal knot 106. Distal end of shape wire 109 may also be anchored to distal tip 108 or mechanically locked with tubing segment 104. Distal assembly 100 defines an atraumatic tip and maintains tension on fiber 100.

Figure 6:
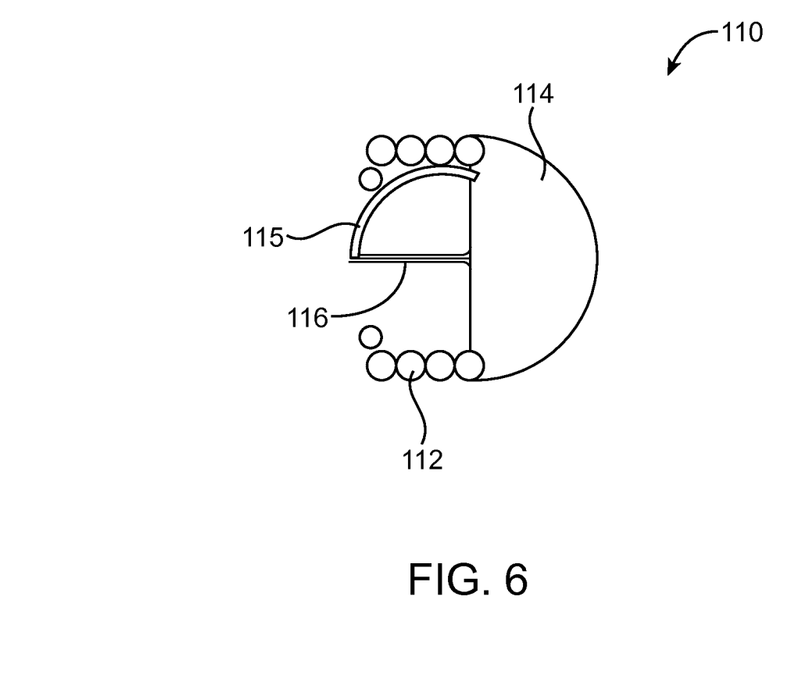
FIG. 6 is a cutaway side view of a distal component of a yet another embodiment according to the invention.

FIG. 6 illustrates the distal end only of another alternative embodiment according to the invention. Distal assembly 110 is disposed at the distal end of primary coil 112, shown in cross section in FIG. 6. A polymer, such as, for example, polypropylene, is melted and reflowed to bond to the distal end of primary coil 112, and to form atraumatic distal tip 114. Also secured to distal tip 114 during the foregoing process are the distal ends of shape wire 115 and fiber 116, which are embedded in distal tip 114.

Figure 7:
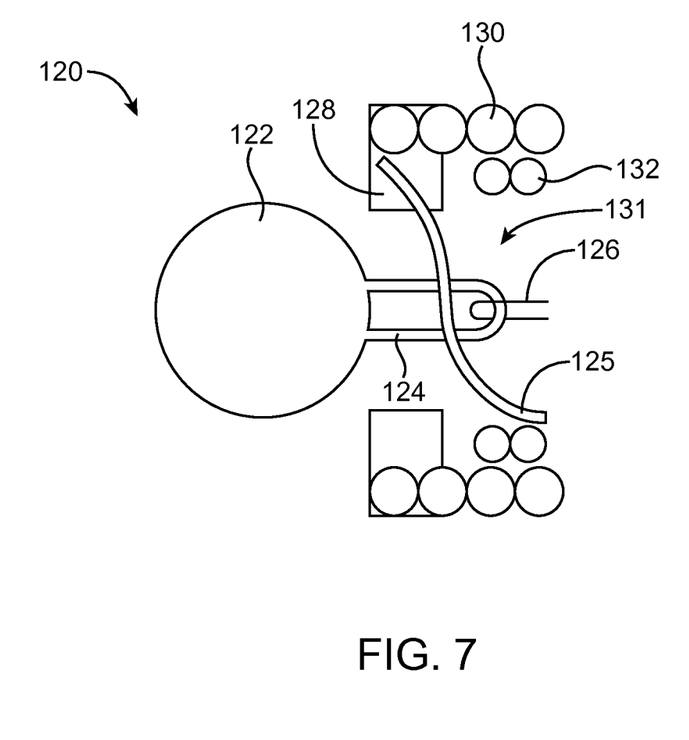
FIG. 7 is cutaway side view of a proximal portion of an embodiment according to the invention.

FIG. 7 illustrates an alternative embodiment of the proximal portion only of an implant according to the invention. Proximal assembly 120 includes proximal sphere 122. Proximal loop 124 is formed from a wire that is formed into a loop, passed through a through hole of proximal sphere 122, and welded to proximal sphere 122. Polymer fiber 126 is in turn looped or threaded through proximal loop 124 to secure fiber 126 to proximal assembly 120. Proximal bond 128 is bonded to the proximal end of primary coil 130, in a fashion similar to the methods described above. Shape wire 125, at its proximal end, is also bonded to or secured by proximal bond 128. Proximal bond 128 prevents proximal sphere 122 from entering lumen 131, and prevents stretching and/or permanent deformation of primary coil 130 and secondary coil 132, the proximal ends of which are shown in FIG. 7.

Figure 8:
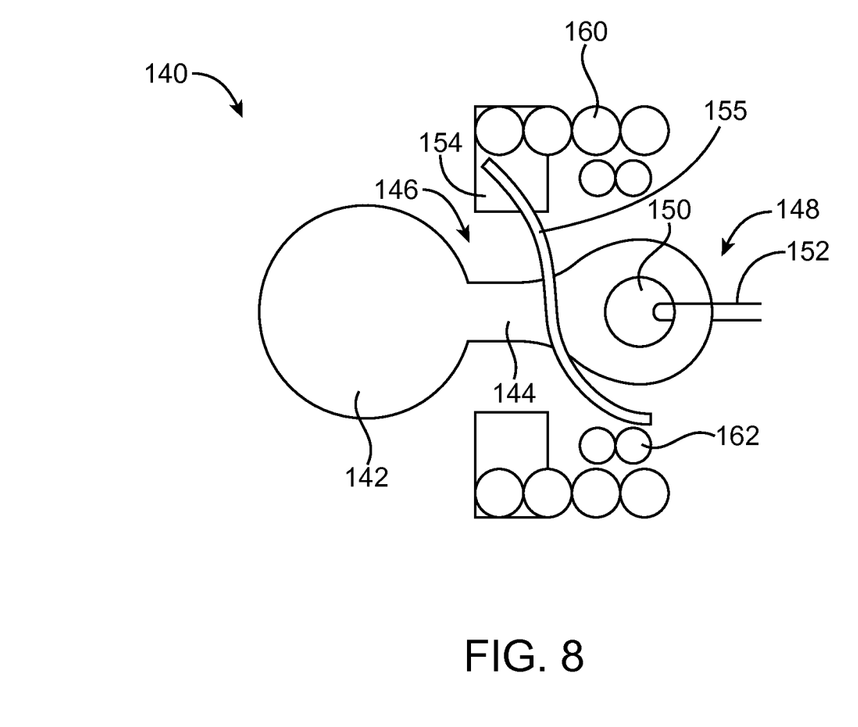
FIG. 8 is a cutaway side view of a proximal portion of an alternative embodiment according to the invention.

FIG. 8 illustrates another embodiment of a proximal assembly according to the invention. Proximal assembly 140 includes proximal constraint sphere 142. Proximal constraint sphere 142 includes a through hole (not visible) through which wire 144 is threaded and then welded to proximal constraint sphere 142. Wire 144 has a proximal end 146 and a distal end 148. At the distal end 148 of proximal assembly 140, wire 144 is flattened and drilled or otherwise processed to form hole 150. Fiber 152 is threaded through hole 150, and looped. Alternatively, two lengths of fiber 152 may be used in order to double the tensile strength of fiber 152. Though not pictured in FIG. 8, fiber 152 extends distally through the lumen of an embolic implant. Proximal bond 154 is formed in a similar fashion to that described above in relation to previously described embodiments, and bonds to the proximal end of primary coil 160 and optionally to the proximal end of shape wire 155. When it is a component of an embolic coil, proximal constraint assembly 140 helps maintain tension on fiber 152 and prevents stretching and/or deformation of the embolic coil.

Figure 9:
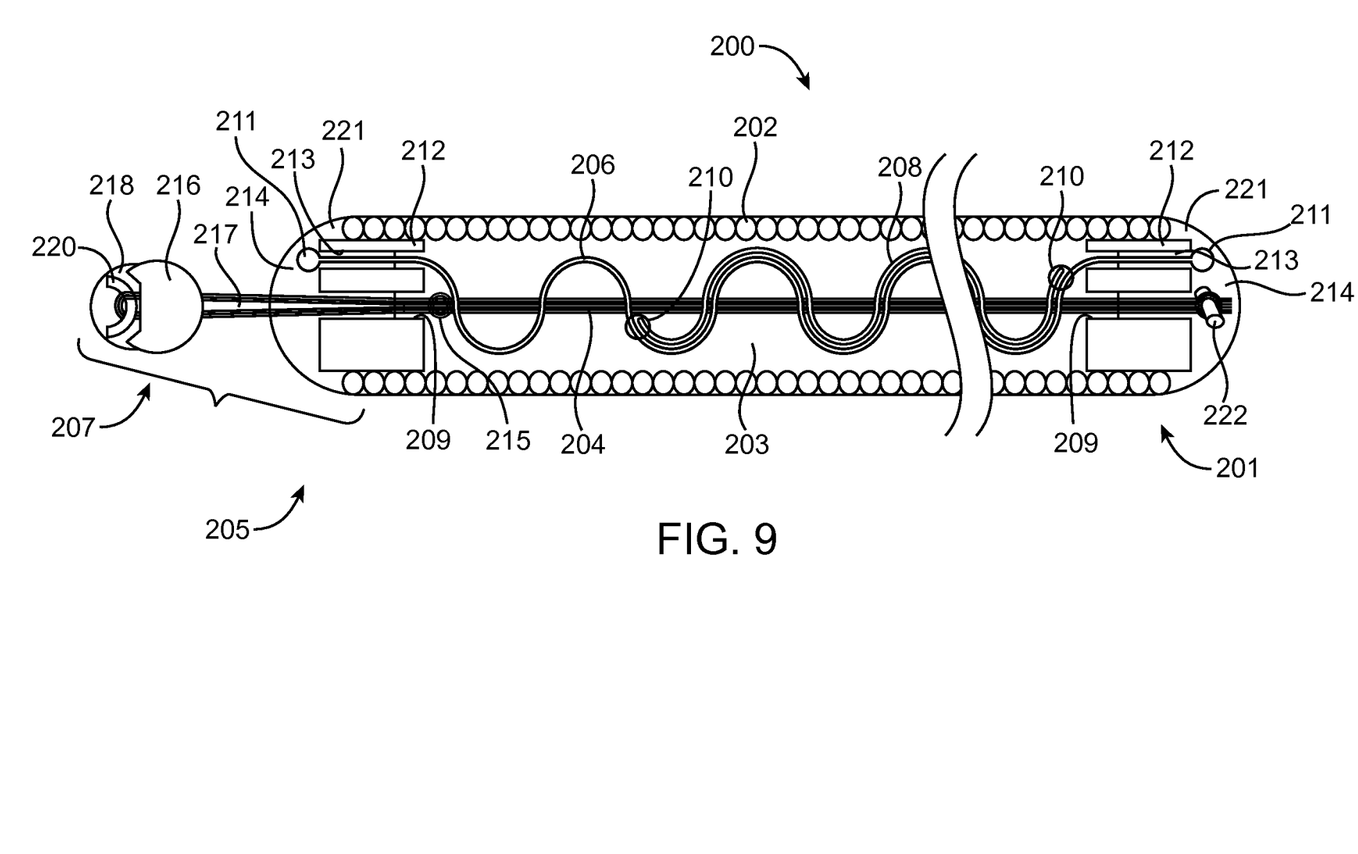
FIG. 9 is a cutaway side view of another alternative embodiment according to the invention.

FIG. 9 illustrates an alternative embodiment of an embolic implant according to the invention. Embolic implant 200 exhibits many advantages over prior art implants, including proximal softness that enhances safety. Embolic implant 200 in particular exhibits progressively increasing softness from its distal end 201 to its proximal end 205. In other words, distal end 201 exhibits a more robust secondary or three dimensional shape than does proximal end 205. And proximal end 205 exhibits greater overall compliance and softness. An implant such as embolic implant 200 can be shape set to, upon release from the constraints of a delivery catheter, return to a shape such as, for example, the configuration illustrated in FIG. 11. FIG. 11 will be discussed in greater detail below.

Embolic implant 200 is shown in cross section in FIG. 9, in order that its features may be readily viewed. Embolic implant 200 includes primary coil 202. Primary coil may be constructed from any of the materials suitable for the coils described above. Primary coil 202 includes an internal lumen 203. Disposed in and extending through lumen 203 is fiber 204. Also disposed in lumen 203 are elliptical hole washers 212, one near proximal end 205 and one near distal end 201. (The term elliptical hole washers is used herein to describe a washer having a round hole and an elliptical hole. It will be understood that any washer having a plurality of holes or apertures may be used to form an embodiment within the scope of the invention.) Fiber 204 is threaded through elliptical holes 209 of elliptical hole washers 212. Fiber 204 also traverses elliptical hole 209 at proximal end 209, extends beyond proximal end 205 and is attached to a proximal constraint assembly 207. Proximal constraint assembly 207 will be described in greater detail below.

Also extending through lumen 203 is primary shape wire 206. Each end of primary shape wire 206 extends through an elliptical hole washer 212, via apertures 213. Further, each end of primary shape wire 206 is optionally flattened or affixed to a broadened element 211 to prevent primary shape wire 206 from passing back through apertures 213. Primary shape wire 206 is most advantageously constructed from Nitinol. Primary shape wire 206 is shape set to confer a secondary shape on embolic implant 200. Coupled to primary shape wire 206 is distal support wire 208. Distal support wire 208 is linked to shape wire 206 towards the distal end 201 of embolic implant 200. In the example of FIG. 9, distal support wire 208 is attached to shape wire 206 at bonds 210. Where it is coupled to distal support wire 208, the stiffness or robustness of shape wire 206 is augmented by distal support wire 208, and both members confer the secondary configuration of embolic implant 200. The absence of distal support wire 208 near proximal end 205 permits primary shape wire 206 to exhibit a softer, less robust secondary shape, and creates the progressively increasing softness of proximal end 205.

Also disposed at each end of primary coil 202 are weld joints 221. In the example of FIG. 9, weld joints 221 are constructed of a Platinum-Platinum bond. Weld joints 221 each anchor elliptical hole washers 212 to primary coil 202. After construction of weld joints 221, atraumatic tips 214 are formed from a molded polymer or adhesive. Fiber 204 is also secured within atraumatic tips 214. Atraumatic tip 214 disposed at distal end 201 also secures distal peg 222, which will be described in greater detail below.

Turning for now to proximal end 205, elliptical hole washer 212 prevents proximal constraint assembly 207 from entering lumen 203. Proximal constraint assembly accordingly helps maintain tension on fiber 204. Several structures define proximal constraint assembly 207. These structures include fiber loop 217, proximal constraint element or proximal constraint sphere 216, adhesive 218, and proximal wire 220. Fiber loop 217 is threaded through a hole in proximal constraint sphere 216. Proximal wire 220 is in turn threaded through the proximal end of loop 217. Loop 217 thereby links proximal constraint sphere 216 and proximal wire 220, and forms a mechanical lock of fiber 204 at proximal end 205. Adhesive 218 is molded or applied to secure proximal wire 220, loop 217, and proximal constraint sphere 216.

Returning now to distal end 201, fiber 204 is threaded distally through embolic implant lumen 203 and then through aperture 209 of washer 212 disposed at distal end 201. Fiber 204 is tied, knotted, or otherwise linked to distal peg 222. Distal peg 222 can be formed from stainless steel, platinum, or other similarly rigid material. Distal peg 222 and fiber 204 are embedded or otherwise anchored or bonded to the distal atraumatic tip 214, forming a mechanical lock adjacent to distal elliptical hole washer 212. Together, proximal constraint assembly 207 and distal peg 222 maintain tension on fiber 204, which thereby enables embolic implant 200 to resist stretching and elongation.

Figure 10:
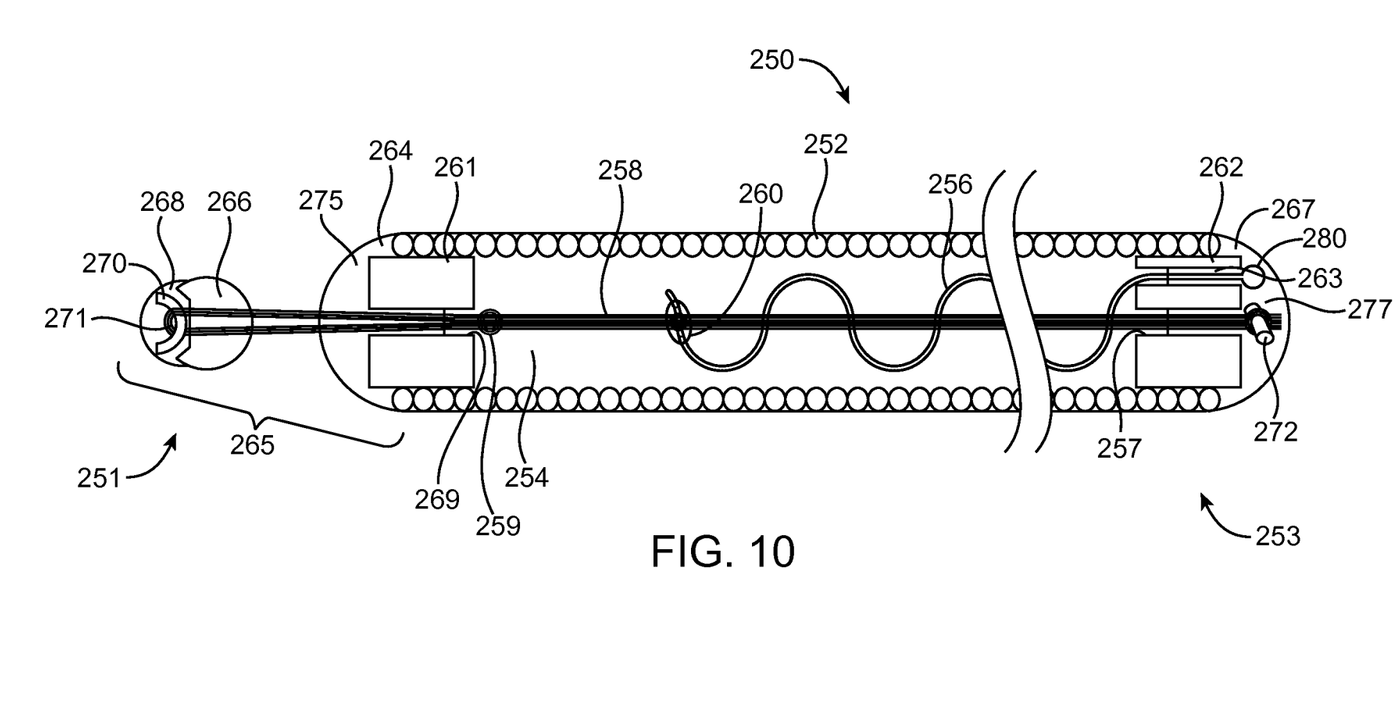
FIG. 10 is a cutaway side view of yet another alternative embodiment according to the invention.

Turning now to FIG. 10, an alternative embodiment according to the invention will be described. Embolic implant 250 is shown in its linear, delivery configuration. Following release from the constraints of a delivery catheter (not pictured), embolic implant will revert to a shape set secondary configuration. The secondary configuration may be any of a number of shapes according to the invention, including the complex shape illustrated in FIG. 1b above, and FIG. 11 described below.

Embolic implant 250 has a proximal end 251 and a distal end 253 Elliptical hole washer 261is disposed at proximal end 251 and elliptical hole washer 262 is disposed at distal end 253. Embolic implant 250 includes a primary coil 252 that is shape set during the manufacturing process to impart a secondary, deployed configuration on embolic implant 250. Primary coil 252 surrounds lumen 254. Disposed within lumen 254 is fiber 258. In a fashion similar to that described in relation to FIG. 9, fiber 258 extends through elliptical hole 257 of elliptical hole washer 262, and through elliptical hole 269 of elliptical hole washer 261. After passing through elliptical hole washer 261, fiber 258 is looped back upon itself to form loop 271, brought into lumen 254, and knotted to itself to form knot 259.

Also disposed within lumen 254 is distal support wire 256. Distal support wire 256 renders the secondary configuration of embolic implant 250 more robust in the distal region in which distal support wire 256 lies. (Embolic implant 250 is more softly shaped near its proximal end 251.) Distal support wire 256 is attached to fiber 258 at bond 260. Distal support wire 256 extends at its distal end through aperture 263 of elliptical hole washer 262. The distal end of distal support wire 256 is optionally flattened to form a broadened element 280, or attached to a broadened element 280, to mechanically lock distal support wire 256 to elliptical hole washer 262.

Weld joint 264 is constructed at proximal end 251 in a fashion similar to that described above, and atraumatic tip 275 is formed from reflowed or molded polymer, adhesive, or a combination thereof. Weld joint 264 anchors primary coil 252 and elliptical hole washer 261 at proximal end 251. At distal end 253, weld joint 267 similarly bonds primary coil 252 and elliptical hole washer 262. A molded or reflowed polymer, adhesive or comparable material forms atraumatic tip 277.

Proximal constraint assembly 265 is similar to the proximal constraint assembly described above in relation to FIG. 9. Proximal constraint element or proximal constraint sphere 266 is linked to fiber 258 and proximal constraint wire 270. Fiber 258 is either threaded through or wrapped around proximal constraint sphere 266 and looped, and proximal constraint wire 270 is threaded through loop 271. Adhesive 268 secures proximal constraint sphere 266, fiber 258 and proximal wire constraint wire 270. Elliptical hole washer 261 prevents proximal constraint sphere 266 from entering lumen 254, and prevents stretching and/or deformation of primary coil 252. At distal end 253, fiber 258 is tied or otherwise coupled to distal peg 272, which is embedded in or otherwise bonded or anchored to distal atraumatic tip 275, Securing fiber 253 to distal peg 272 helps maintain tension on fiber 258.

As mentioned above, embolic implant 250 can be shape set to revert to a secondary configuration such as the configuration illustrated in FIG. 1B above. An advantageous step in shape setting implant 250 includes the step of shape setting primary coil 252. Primary coil 252 is first formed by winding or otherwise forming continuous turns of a length of Platinum wire about a straight mandrel. The coiled wire can then be heat set to "remember" the primary coil shape. The Platinum primary coil formed from continuous turns can then be shaped around a fixture bearing a desired secondary shape. The Platinum primary coil is then heat set to "remember" the shape of the fixture. Of particular advantage in forming a low profile coil that readily fills empty space within an aneurysm or within a frame defined by another implant, is utilizing a fixture around which the primary coil turns are wrapped. In other words, the fixture is disposed within the lumen of the primary coil during the heat setting step, instead of the primary coil being first coiled, and then wrapped around the exterior of the fixture. Such a step results in smaller primary diameter coils and lower profile secondary configurations.

Turning now to FIG. 11, an embodiment according to the invention will be described. While FIG. 1b above illustrates an example of a complex secondary shape of an implant according to the invention, FIG. 11 illustrates an alternative complex secondary shape, or secondary configuration of an embolic implant constructed according to the invention. FIG. 11 illustrates a plan, or topside view of implant 300 in its deployed configuration, outside a vessel of a subject, such as, for example, on a laboratory bench top. Similar to the embodiments described above, the embodiment illustrated in FIG. 11 also has a delivery configuration, similar to that illustrated in FIG. 9, that is generally linear, that permits the device to be loaded into and delivered via a catheter or comparable delivery tool (not pictured). In its secondary configuration outside a vessel, implant 300 has a proximal segment 302. Proximal segment 302 is shaped by a relatively soft or flexible shape wire (not visible in FIG. 11). The shape wire imparting the secondary shape to proximal segment 302 is soft or flexible either because of a small diameter, a fine grind, or other processing step which produces a relatively soft filament. A wide range of flexibility, or softness, of the filament is within the scope of the invention, and the term "relatively" is used here to mean in comparison to distal segment 304, which will be discussed below.

Proximal segment 302 has a secondary (or deployed) configuration, outside of a vessel that is helical. Alternatively, a proximal segment may have a secondary configuration that is complex, similar to the secondary configuration of distal segment 304, described in more detail below. In yet another alternative embodiment, a proximal segment according to the invention may have a straight or linear configuration. Though a wide range of outer diameters of the helix of proximal segment 302 are within the scope of the invention, in the example illustrated here, the outer diameter of proximal segment 302 is approximately 2-30 mm. In a preferable embodiment, the outer diameter of proximal segment 302 is less than the outer diameter of distal segment 304, when both proximal segment 302 and distal segment 304 are in their secondary configurations. Techniques for forming the secondary configuration of proximal segment 302 are known in the art, and include, for example, wrapping the shape wire disposed within proximal segment 302 around a mandrel and heat treating the segment so that it will return via shape memory behavior to the helical shape. Alternative techniques for achieving the shape memory objective are within the scope of the invention.

Implant 300 also has a distal segment 304, as mentioned above. Distal segment 304 also includes, disposed within its interior and therefore not visible in FIG. 11, a shape wire that is fabricated from a wire, filament, or comparable structure that is stiffer relative to that used to fabricate proximal segment 302. (Alternatively, a coil may be shape set to return to the configuration of FIG. 11 upon release from a constraint.) The shape of distal segment 304 may be formed from a wire or filament that is of greater thickness than that used to fabricate proximal segment 302, in a fashion similar to that described in relation to FIG. 2 above. As another example, distal segment 304 may include, similar to that pictured in FIG. 9 above, a support wire coupled to the shape wire, the support wire extending only the length of distal segment 304. As yet another example, additional processing steps such as annealing or other steps may be undertaken with respect to the material used to fabricate the filament that forms the support wire of distal segment 304. Regardless of the technique used to manufacture the shape wire of distal segment 304, the resulting secondary structure is a stiffer or more robust three dimensional object than that of proximal segment 302.

In addition, as can be viewed in FIG. 11, distal segment 304 has a secondary configuration that is more complex than the generally helical shape of proximal segment 302. In an alternative embodiment according to the invention, a distal segment may have a secondary configuration that is helical, similar to the secondary configuration described in more detail above, in relation to the description of proximal segment 302. In the example illustrated in FIG. 11, the deployed shape of distal segment 304 is characterized as having sides 306, top 308, and bottom 312. Taken together, sides 306, top 308, and bottom 312 generally define a cubic shape having rounded corners. Therefore, distal segment 304 can be described as having the shape of a cube. The term "cube" is used here to denote a three dimensional shape having several faces, and a particular embodiment according to the invention may or may not have six faces. The corners and edges of each face may be squared or rounded, curved or straight. Each face may or may not be of equal dimensions as each other face. Further, as is visible in FIG. 11, the secondary shape of distal segment 304 frames some open "interior" space, and much of the coiled element defines the outer edges of the secondary shape of distal segment 304.

In addition to having a very different secondary shape than proximal segment 302, distal segment 304 also has a larger outside profile or outer diameter than proximal segment 302. For example, in the embodiment illustrated in FIG. 11, distal segment 304 has an outer diameter of approximately 3-32 mm. Techniques for shaping distal segment 304 include a series of steps of wrapping the stretch resistant member of distal segment 304 around a specialized mandrel or comparable tool, and heat treating the distal wire member so that it returns to the secondary shape imparted by the tool. Alternative techniques for fabricating the stretch resistant member disposed within distal segment 304 are within the scope of the invention.

The combination of both this larger outer diameter, the concentration of material at the outer edges of the shape, and the stiffer internal wire of distal segment 304 cause distal segment 304 to function much like an "anchor" for implant 300 within a vessel. In other words, distal segment 304 exerts some outward radial force against a vessel wall when implant 300 is deployed within a vessel. And, when deployed within a blood vessel of a subject, blood flow may carry proximal segment into the "interior" or distal segment 304, filling distal segment 304, and effectively preventing further blood flow through implant 300. In this respect, implant 300 effectively has an "anchor" segment and a "filler" segment, resulting in a soft, well packed embolic implant.

Figure 12:
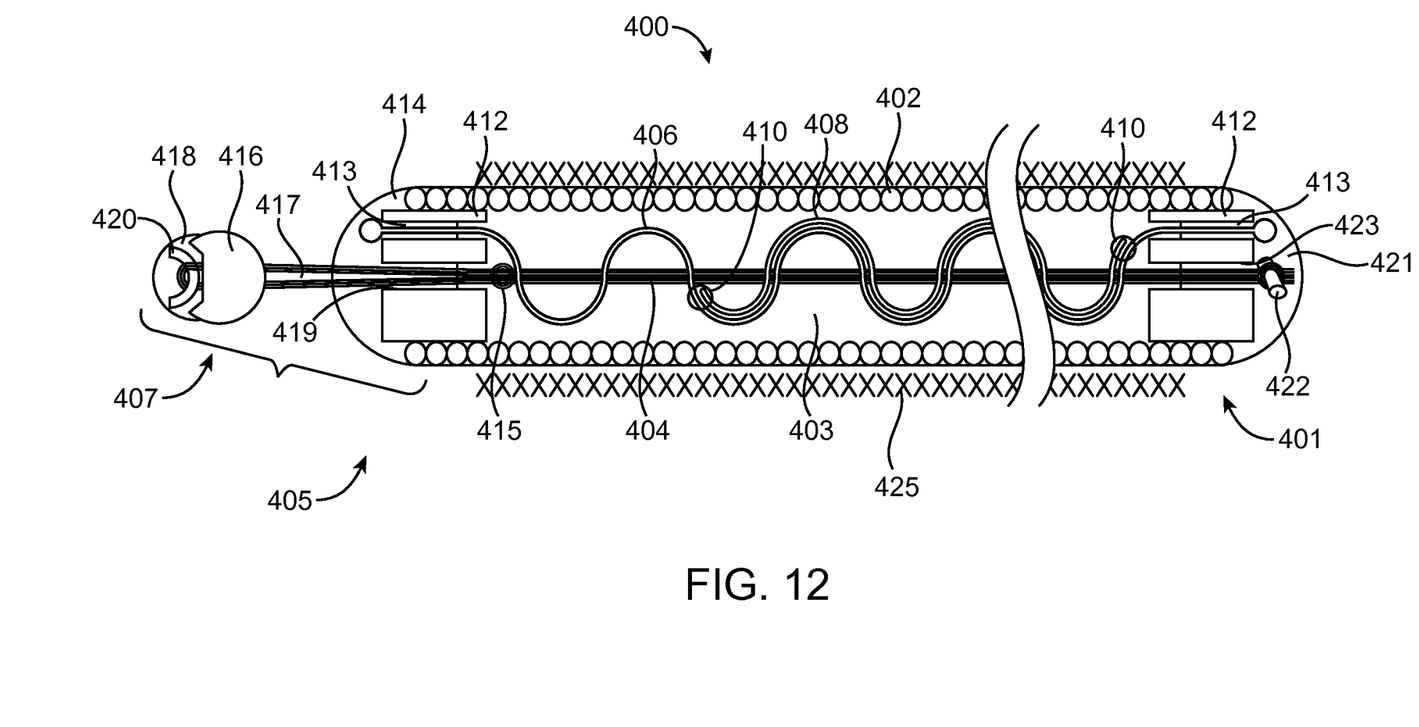
FIG. 12 is a cutaway side view of an alternative embodiment according to the invention.

Turning now to FIG. 12, yet another alternative embodiment according to the invention will be described. Embolic implant 400 shares many of the same features of the embolic implant illustrated in FIG. 9. Embolic implant 400 exhibits many advantages over prior art implants, including softness that enhances safety. Embolic implant 400 in particular boasts the feature of progressively increasing softness from its distal end 401 to its proximal end 405. In other words, distal end 401 exhibits a more structured secondary or three dimensional shape than proximal end 405. And proximal end 405 exhibits greater overall compliance and softness. An implant such as embolic implant 400 can be shape set to, upon release from the constraints of a delivery catheter, return to a secondary shape such as, for example, the configuration illustrated in FIG. 11 above.

Embolic implant 400 is shown in cross section in FIG. 12, in order that its features may be readily viewed. Embolic implant 400 has a primary diameter of approximately 0.018 inches. Embolic implant includes primary coil 402. Primary coil may be constructed from any of the materials suitable for coils described above. Primary coil 402 includes an internal lumen 403. Primary coil 403 is shape set to exhibit a secondary shape following release from a delivery catheter (not pictured). Primary coil 403 may be constructed from Platinum or other suitable shape memory material. Extending through lumen 403 is fiber 404. Fiber 404 also extends beyond proximal end 405 and is attached to a proximal constraint assembly 407. Proximal constraint assembly 407 will be described in greater detail below. Also extending through lumen 403 is primary shape wire 406. Primary shape wire 406 is most advantageously constructed from Nitinol. Coupled to primary shape wire 406 is distal support wire 408. Distal support wire 408 is linked to primary shape wire 406 towards the distal end 401 of embolic implant 400. The stiffness of shape wire 406 is augmented by distal support wire 408, and both members confer the secondary configuration on embolic implant 400. The absence of distal support wire 408 at proximal end 405 creates the progressive softness of proximal end 405. In the example of FIG. 12, distal support wire 408 is bonded to primary shape wire 406 at bonds 410.

As mentioned above, primary shape wire 406 extends essentially the length of embolic implant 400. Each end of shape wire 406 extends through an elliptical hole washer 412, via apertures 413. Elliptical hole washers 412 are disposed at each end of primary coil 402. Also disposed at each end of primary coil 402 is a molded polymer or adhesive 421, each of which secures elliptical hole washers 412 to primary coil 402 and fiber 404, and forms atraumatic tips 414. Both proximal end 405 and distal end 401 have atraumatic tips 414.

Several structures define proximal constraint assembly 407. As mentioned above, fiber 404 extends beyond proximal end 405. Fiber 404 is looped back onto itself to form loop 417. After forming loop 417, fiber 404 extends back into lumen 403, and is secured to itself via knot 415. Loop 417 links proximal constraint sphere 416 and proximal wire 420. Adhesive 418 is molded or applied to secure proximal wire 420, loop 417, and proximal constraint sphere 416. Elliptical hole washer 412 and adhesive 421 prevent proximal constraint sphere 416 from entering lumen 403.

Extending distally through lumen 403, fiber 404 is tied, knotted, or otherwise linked to distal peg 422. Distal peg 422 and fiber 404 are embedded or otherwise anchored to the distal atraumatic tip 414. Together, proximal constraint assembly 407 and distal peg 422 maintain tension on fiber 404, which thereby enables embolic implant 400 to resist stretching and plastic deformation.

Unlike the embodiment of FIG. 9, embolic implant 400 also includes jacket 425. Jacket 425 wraps or encases primary coil 402. Jacket 425 is preferably constructed from a thrombogenic material such as polyester, polypropylene, silk, or other suitable material. The thrombogenic material or materials may be monofilament or multi-filament fibers. Jacket 425 may be constructed by wrapping, winding, braiding, threading or otherwise arranging the fiber or fibers in engagement with coil 402. Jacket 425 may be constructed to form a "sleeve" like structure that is placed over coil 402, or applied directly to coil 402 to form jacket 425.

The foregoing examples are not intended to limit the scope of the invention. All modifications, equivalents and alternatives are within the scope of the invention. As an example, a proximal constraint element or a distal constraint element according to the invention need not be a sphere, but may be a disc, a block, a tear drop, or of any suitable alternative shape.

We claim:

1. An embolic implant comprising:
    a proximal end and a distal end;
    a first coil having a length and comprising a lumen extending through said first coil;
    a non-stretch resistant shape memory filament and a stretch resistant fiber without shape memory disposed in said lumen, wherein the shape memory filament and the stretch resistant fiber both extend for at least the entire length of the first coil;
    a second coil disposed in said lumen;
    a proximal constraint assembly disposed at said proximal end; and
    a distal assembly disposed at said distal end, wherein said shape memory filament comprises a first, constrained linear configuration and a second configuration comprised of a segmented series of shapes that are proximally helical and distally cubic.

2. The embolic implant according to claim 1, wherein said second coil comprises shape memory material, and said second coil comprises a first, constrained linear configuration and a second configuration that is helical, J-shaped, spherical, complex, cubic, or a segmented combination of shapes.

3. The embolic implant according to claim 1, said implant further comprising a proximal bond disposed at the proximal end, wherein said proximal bond is affixed to said first coil, said shape memory filament, or both.

4. The embolic implant according to claim 3, wherein said proximal bond is annular or solid.

5. The embolic implant according to claim 1, wherein the second configuration is helical for a first portion of the length of the first coil and cubic for a remaining, more distal portion of the length of the first coil.

6. The embolic implant according to claim 5, the implant further comprising a distal constraint element having a through hole, wherein said stretch resistant fiber is disposed through said through hole and knotted to form a distal knot.

7. The embolic implant according to claim 6, said implant further comprising a distal tip disposed at the distal end of said first coil, wherein said distal tip comprises a polymer, or an adhesive or both, said stretch resistant fiber is knotted to form a distal knot, and said distal constraint element and said distal knot are embedded in said polymer or said adhesive or both.

8. The embolic implant according to claim 1, wherein said stretch resistant fiber comprises a first proximal knot, said proximal constraint assembly includes a proximal constraint element configured to be releaseably retained by a delivery device, wherein said proximal constraint element comprises a through hole and said stretch resistant fiber is disposed through said through hole.

9. The embolic implant according to claim 8, said embolic implant further comprising a solid proximal bond, wherein said stretch resistant fiber is knotted to form a second proximal knot, and said second proximal knot is secured to said solid proximal bond.

10. The embolic implant according to claim 1, the implant further comprising a distal tip disposed at the distal end of the first coil.

11. The embolic implant according to claim 10, wherein said distal tip comprises a polymer, or an adhesive, or both, said stretch resistant fiber is knotted to form a distal knot, and said distal knot is embedded in said polymer or said adhesive or both.

12. The embolic implant according to claim 11, said implant further comprising a tube segment having a lumen and disposed at said distal end, wherein said stretch resistant fiber is disposed through said lumen, said distal knot is disposed distal to said tube segment, and said tube segment and said distal knot are embedded in said polymer or said adhesive or both.

13. The embolic implant according to claim 1 wherein said proximal constraint assembly comprises a proximal constraint element having a distal aperture, said stretch resistant fiber engages said distal aperture.

14. The embolic implant according to claim 1 wherein said shape memory filament comprises a proximal end, a distal end and a variable diameter, and said variable diameter varies from a lesser diameter near said proximal end to a greater diameter near said distal end.

* * * * *